(12) United States Patent
Hathaway et al.

(10) Patent No.: US 12,329,392 B2
(45) Date of Patent: Jun. 17, 2025

(54) CANNULATED, MODULAR FEMORAL BROACH AND SURGICAL INSTRUMENT HANDLE

(71) Applicant: DEPUY IRELAND UNLIMITED COMPANY, Ringaskiddy (IE)

(72) Inventors: Tyler S. Hathaway, Auburn, IN (US); Adam L. Carver, Raleigh, NC (US); Kyle D. Steffe, Warsaw, IN (US); Aaron J. Matyas, Fort Wayne, IN (US); Anthony J. Webb, Fort Wayne, IN (US); Craig S. Tsukayama, Fort Wayne, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 277 days.

(21) Appl. No.: 18/140,814

(22) Filed: Apr. 28, 2023

(65) Prior Publication Data

US 2023/0263539 A1 Aug. 24, 2023

Related U.S. Application Data

(62) Division of application No. 16/729,355, filed on Dec. 28, 2019, now Pat. No. 11,648,016.

(51) Int. Cl.
*A61B 17/16* (2006.01)
(52) U.S. Cl.
CPC ........ *A61B 17/164* (2013.01); *A61B 17/1675* (2013.01); *A61B 2560/0443* (2013.01)
(58) Field of Classification Search
CPC .............. A61B 17/164; A61B 17/1675; A61B 2560/0443
See application file for complete search history.

(56) References Cited

U.S. PATENT DOCUMENTS

| 5,006,121 A | 4/1991 | Hafeli |
| 5,601,564 A | 2/1997 | Gustilo et al. |
| 5,607,431 A | 3/1997 | Dudasik et al. |
| 5,800,437 A | 9/1998 | Gustilo et al. |
| 5,908,423 A * | 6/1999 | Kashuba .............. A61B 17/175 |
| | | 408/127 |
| 6,117,138 A | 9/2000 | Burrows et al. |
| 9,113,918 B2 | 8/2015 | Chaney et al. |

(Continued)

FOREIGN PATENT DOCUMENTS

| BE | 1015812 A3 | 9/2005 |
| CN | 104042303 A | 9/2014 |

OTHER PUBLICATIONS

Extended European Search Report for European Patent Application No. 20217307.6, Oct. 22, 2021, 20 pages.

(Continued)

*Primary Examiner* — Sameh R Boles
(74) *Attorney, Agent, or Firm* — Barnes & Thornburg LLP

(57) ABSTRACT

An orthopaedic surgical instrument assembly includes a surgical reamer, a cannulated broach, and an instrument handle. The broach includes a bore sized to slide over a shaft of the reamer. The handle attaches to the broach and also includes a bore sized to slide over a shaft of the reamer. A modular broach assembled from a number of broach segments may be used. Methods associated with the surgical instrument assembly are also disclosed.

6 Claims, 12 Drawing Sheets

(56) References Cited

U.S. PATENT DOCUMENTS

| | | |
|---|---|---|
| 2003/0220698 A1 | 11/2003 | Mears et al. |
| 2005/0234462 A1* | 10/2005 | Hershberger ......... A61F 2/4637 606/85 |
| 2013/0172892 A1 | 7/2013 | Servidio et al. |
| 2015/0359546 A1 | 12/2015 | Thomas et al. |
| 2017/0290596 A1 | 10/2017 | Kelman et al. |
| 2019/0099191 A1 | 4/2019 | Huff et al. |
| 2019/0110906 A1 | 4/2019 | Yoko et al. |
| 2019/0110909 A1 | 4/2019 | Sverrisson et al. |
| 2019/0201010 A1 | 7/2019 | Wogoman et al. |
| 2019/0201012 A1 | 7/2019 | Sitry et al. |
| 2021/0196285 A1 | 7/2021 | Hathaway et al. |

OTHER PUBLICATIONS

Chinese Search Report for CN Application No. 2020115664049 dated Dec. 6, 2024, 19 pages.

\* cited by examiner

CANNULATED, MODULAR FEMORAL BROACH AND SURGICAL INSTRUMENT HANDLE

CROSS-REFERENCE TO RELATED APPLICATIONS

The present application is a divisional application of U.S. application Ser. No. 16/729,355, now U.S. Pat. No. 11,648,016, entitled "CANNULATED, MODULAR FEMORAL BROACH AND SURGICAL INSTRUMENT HANDLE," which was filed on Dec. 28, 2019, the entirety of which is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, broaches, drill guides, prosthetic trials, and other surgical instruments to prepare the patient's bones to receive the knee prosthesis.

SUMMARY

According to one aspect of the disclosure, an orthopaedic surgical instrument system includes a broach having a tapered body extending distally from a first end to a second end, the tapered body having a plurality of cutting teeth defined therein. The broach includes an inner wall defining a first aperture on the first end and a second aperture on the second end, and a bore sized to slide over a shaft of a surgical reamer that extends from the first aperture to the second aperture.

In an embodiment, the orthopaedic surgical instrument system further includes an instrument handle having an elongated body extending distally from a first end to strike plate. The instrument handle includes an inner wall defining a third aperture on the first end of the instrument handle and a bore sized to slide over the shaft of the surgical reamer that extends distally from the third aperture into the elongated body. In an embodiment, the second end of the broach is configured to be removably secured to the first end of the instrument handle. In an embodiment, the broach includes a flange positioned within a slot defined in the second end of the broach, and the instrument handle includes a hook positioned at the first end of the instrument handle and configured to engage the flange of the broach.

In an embodiment, the orthopaedic surgical instrument system further includes the surgical reamer. The surgical reamer includes a cutting head coupled to an elongated shaft. The elongated shaft is sized to be received within the bore of the broach.

According to another aspect, an orthopaedic surgical instrument assembly includes a first broach segment and a second broach segment. The first broach segment includes a tapered body extending from a proximal end to a distal end, the tapered body having a plurality of cutting teeth defined therein, and the second broach segment includes a tapered body extending from a proximal end to a distal end, the tapered body having a plurality of cutting teeth defined therein. The proximal end of the second broach segment is removably coupled to the distal end of the first broach segment. When coupled, the first broach segment and the second broach segment cooperate to define a bore that extends from a first aperture defined in the proximal end of the first broach segment to a second aperture defined in the distal end of the second broach segment, wherein the bore is sized to slide over a shaft of a surgical reamer. When coupled, the tapered body of the first broach segment and the tapered body of the second broach segment form a tapered outer surface that widens from the proximal end of the first broach segment to the distal end of the second broach segment.

In an embodiment, the second broach segment includes a dovetail positioned on the proximal end of the second broach segment, and a dovetail slot is defined in the distal end of the first broach segment. The dovetail slot is sized to receive the dovetail of the second broach segment. In an embodiment, the first broach segment includes a ball detent positioned on the distal end of the first broach segment, and a recess is defined in the proximal end of the second broach segment, wherein the recess is sized to receive the ball detent of the first broach segment. In an embodiment, the distal end of the first broach segment and the distal end of the second broach segment are each configured to be removably attached to a surgical instrument handle.

In an embodiment, the orthopaedic surgical instrument assembly further includes a third broach segment having a tapered body extending distally from a proximal end to a distal end, the tapered body having a plurality of cutting teeth defined therein, wherein the proximal end of the third broach segment is removably coupled to the distal end of the second broach segment. When the third broach segment is coupled to the second broach segment, the bore further extends to an aperture defined in the distal end of the third broach segment, and the tapered body of the third broach segment extends the tapered outer surface that widens from the proximal end of the first broach segment to the distal end of the third broach segment.

In an embodiment, the orthopaedic surgical instrument assembly further includes a fourth broach segment having a tapered body extending distally from a proximal end to a distal end, the tapered body having a plurality of cutting teeth defined therein, wherein the proximal end of the fourth broach segment is removably coupled to the distal end of the third broach segment. When the fourth broach segment is coupled to the third broach segment, the bore further extends to an aperture defined in the distal end of the fourth broach segment, and the tapered body of the fourth broach segment extends the tapered outer surface that widens from the proximal end of the first broach segment to the distal end of the fourth broach segment.

In an embodiment, the orthopaedic surgical instrument assembly further includes a fifth broach segment having a tapered body extending distally from a proximal end to a distal end, the tapered body having a plurality of cutting teeth defined therein, wherein the proximal end of the fifth broach segment is removably coupled to the distal end of the fourth broach segment. When the fifth broach segment is coupled to the fourth broach segment, the bore further extends to an aperture defined in the distal end of the fifth broach segment, and the tapered body of the fifth broach segment extends the tapered outer surface that widens from the proximal end of the first broach segment to the distal end of the fifth broach segment.

In an embodiment, the orthopaedic surgical instrument assembly further includes a sixth broach segment having a tapered body extending distally from a proximal end to a distal end, the tapered body having a plurality of cutting teeth defined therein, wherein the proximal end of the sixth broach segment is removably coupled to the distal end of the fifth broach segment. When the sixth broach segment is coupled to the fifth broach segment, the bore further extends to an aperture defined in the distal end of the sixth broach segment, and the tapered body of the sixth broach segment extends the tapered outer surface that widens from the proximal end of the first broach segment to the distal end of the sixth broach segment.

According to another aspect, a method of performing an orthopaedic surgical procedure on a distal end of a patient's femur includes advancing a cutting head of a surgical reamer into a medullary canal of a patient's surgically prepared femur, wherein the surgical reamer further includes an elongated shaft coupled to the cutting head, sliding a bore defined through the broach over the elongated shaft in response to advancing the cutting head into the medullary canal, wherein the bore defined through the broach extends from a proximal end of the broach to a distal end of the broach, and advancing the broach into the medullary canal in response to sliding the bore defined through the broach over the elongated shaft.

In an embodiment, the method further includes attaching the distal end of the broach to an instrument handle, wherein advancing the broach includes impacting a strike plate of the instrument handle. In an embodiment, the method further includes sliding a bore defined in the instrument handle over the elongated shaft after sliding the bore of the broach over the elongated shaft, wherein the bore defined in the instrument handle extends distally from a first end of the handle.

In an embodiment, the method further includes sliding a bore defined through a broach segment over the elongated shaft, wherein the bore defined through the broach segment extends distally from a proximal end of the broach segment to a distal end of the broach segment, and wherein the proximal end of the broach segment contacts the distal end of the broach, and advancing the broach segment into the medullary canal in response to sliding the bore defined through the broach shaft over the elongated shaft.

In an embodiment, the method further includes attaching the proximal end of the broach segment to the distal end of the broach in response to sliding the bore defined through the broach segment over the elongated shaft, wherein advancing the broach segment includes advancing the broach segment in response to attaching the proximal end of the broach segment.

In an embodiment, the method further includes removing the broach from the medullary canal in response to advancing the broach into the medullary canal, and attaching the proximal end of the broach segment to the distal end of the broach in response to removing the broach from the medullary canal. In an embodiment, sliding the bore defined through the broach segment over the elongated shaft includes sliding the bore defined through the broach and the bore defined through the broach segment over the elongated shaft in response to attaching the proximal end of the broach segment to the distal end of the broach.

BRIEF DESCRIPTION OF THE DRAWINGS

The detailed description particularly refers to the following figures, in which.

DETAILED DESCRIPTION OF THE DRAWINGS

Figure 1:
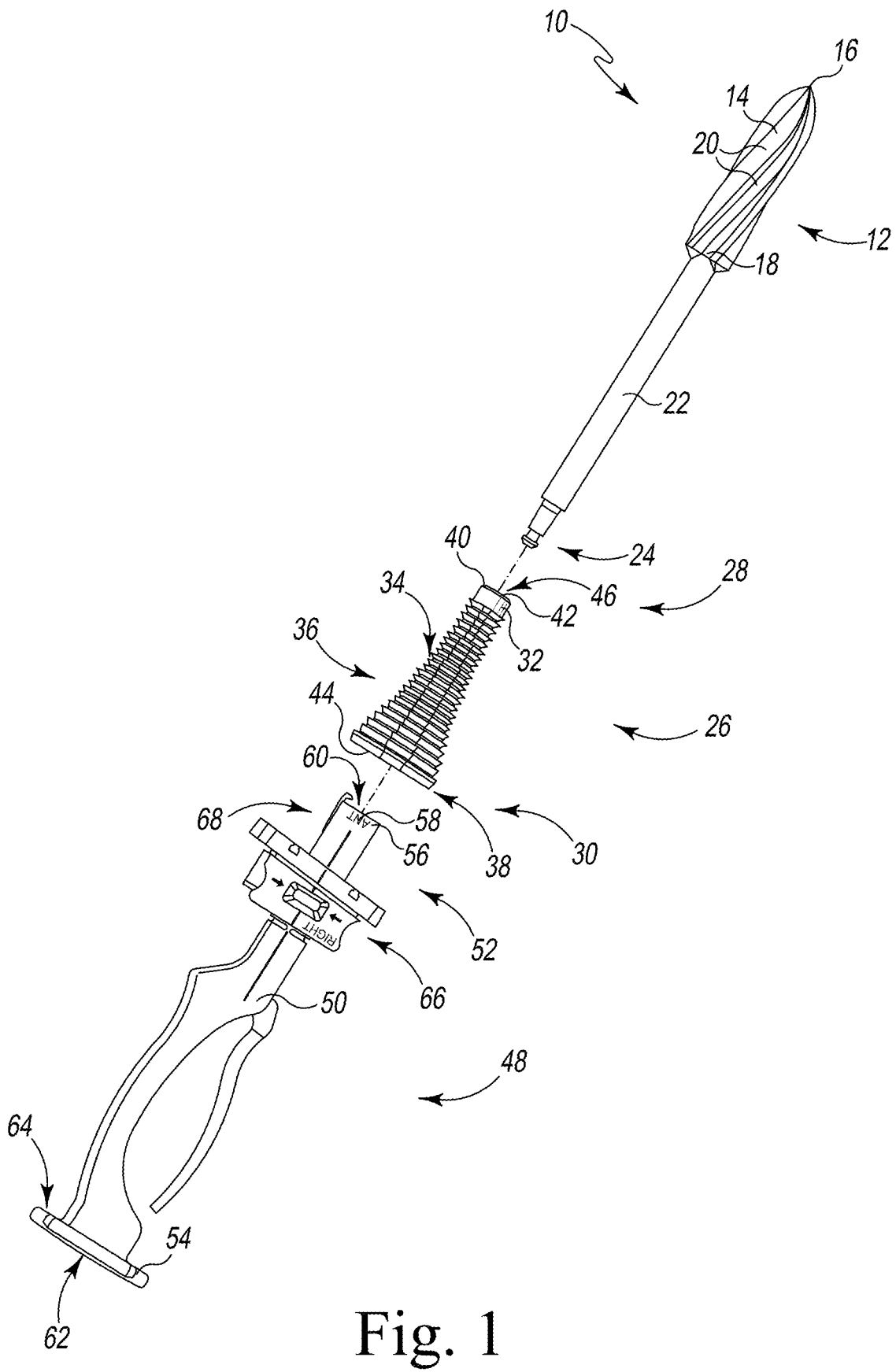
FIG. 1 is an exploded perspective view of a group of orthopaedic surgical instruments of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
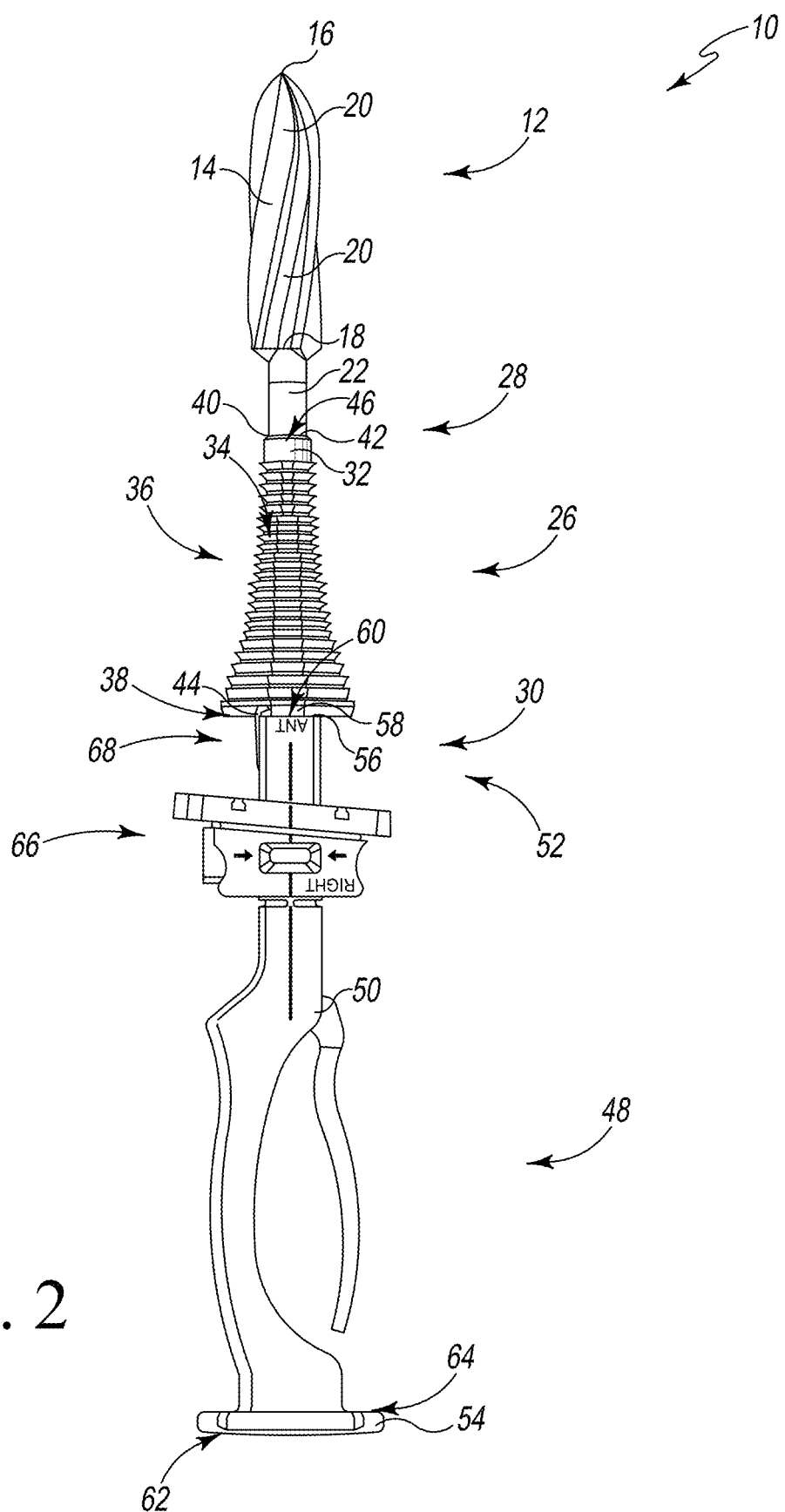
FIG. 2 is a perspective view of the group of orthopaedic surgical instruments of FIG. 1.

Referring now to FIGS. 1 and 2, a group of orthopaedic surgical instruments of an orthopaedic surgical instrument system 10 (hereinafter instrument system 10) is shown. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient.

The system 10 includes a surgical reamer 12, a cannulated broach 26, and an instrument handle 48. As described in greater detail below, a surgeon may use the system 10 in an orthopaedic procedure to prepare a patient's distal femur to receive a femoral implant, for example during a knee revision procedure. In use, the surgeon reams the medullary canal of the patient's femur using the reamer 12. With the reamer 12 remaining in the femoral canal, the surgeon slides the cannulated broach 26 and handle 48 over the reamer 12 and then impacts the handle 48 to advance the broach 26 into the patient's femur. During impaction, the reamer 12 guides the broach 26 into the correct position within the patient's femur. After broaching is completed, the surgeon may then remove the broach 26 and the reamer 12 and install a sleeved femoral component or other prosthesis in the patient's femur. Thus, the system 10 allows the surgeon to broach the patient's femur without attaching a stem trial, stem pilot, or other intramedullary instrument to the proximal end of the broach 26. Accordingly, the system 10 may reduce the risk of damage to the stem trial during impaction (e.g., reduce risk of damage to threaded connections) as compared to conventional systems. Further, although illustrated in the present disclosure as a femoral broach 26, it should be understood that the concepts of this disclosure may also be applied to other surgical instruments, including tibial broaches or other broaches.

In the illustrative embodiment, each instrument of the instrument system 10 is formed from a metallic material, such as, for example, stainless steel or cobalt chromium. The surgical reamer 12 includes a cutting head 14 and an elongated shaft or shank 22 secured to the cutting head 14. The cutting head 14 extends from a tip 16 to a distal base 18 that is coupled to the shaft 22. As shown, the shaft 22 of the surgical reamer 12 has a distal end 24 that fits into a manual handle or the chuck of a rotary power tool.

The cutting head 14 of the reamer 12 includes a plurality of cutting flutes 20 extending between the tip 16 and the base 18. When the surgical reamer 12 is positioned in the medullary canal 82 (see FIG. 3) of the patient's femur and rotated, the cutting flutes 20 of the cutting head 14 ream or otherwise cut the bone tissue of the femur. In the illustrative embodiment, the tip 16 of the cutting head 14 is conical. It should be appreciated that other reamers having cutting heads of different configurations may be provided. For example, the outer diameter of the cutting head may vary to produce reamed canals sized to accommodate prosthetic components of different sizes. Additionally, the length of the cutting head may vary to change the depth of the reamed canal.

As described above, the instrument system 10 includes the cannulated broach 26, which is illustratively a femoral broach configured to be positioned in the medullary canal 82 of the patient's femur. The broach 26 includes an outer surface 34 extending from a proximal end 28 to a distal end 30. The outer surface 34 is tapered, with the diameter of the broach 26 increasing from the proximal end 28 to the distal end 30.

A plurality of cutting teeth 36 are formed on the outer surface 34 between the proximal end 28 and the distal end 30. As described in greater detail below, the cutting teeth 36 are configured to engage the bone surrounding the medullary canal 82 when the broach 26 is inserted therein. It should be appreciated that multiple broaches 26 having different configurations may be provided in the instrument system 10. For example, the outer diameter and/or length of each broach 26 may vary to produce different sized canals to accommodate prosthetic components of different sizes.

The broach 26 includes a boss 32 positioned at the proximal end 28, and includes a substantially planar distal surface 38 positioned at the distal end 30 thereof. The boss 32 at the proximal end 28 has a circular aperture 40 defined therein, and a circular aperture 44 is defined in the distal surface 38. An inner wall 42 extends between the proximal end 28 and the distal end 30, and defines the apertures 40, 44. Accordingly, the inner wall 42 defines a bore 46 that extends through the broach 28 from the proximal end 28 to the distal end 30. The bore 46 is sized to receive and slide over the shaft 22 of the reamer 12 (as well as the distal end 24 thereof).

As described above, the instrument system 10 includes the instrument handle 48, which includes an elongated body 50 that extends from a proximal end 52 to a distal strike plate 54. The proximal end 52 has an aperture 56 defined therein. An inner wall 58 extends inwardly from the proximal end 52 and defines the aperture 56. The inner wall 58 defines a bore 60 that extends inwardly from the proximal end 52 through the body 50. Similar to the bore 46, the bore 60 is sized to receive and slide over the shaft 22 of the reamer 12. As described further below, the bore 60 extends deep enough within the body 50 to contain the shaft 22 when the broach 26 is fully seated within the patient's femur. In the illustrative embodiment, the bore 60 does not extend entirely through the body 50 to the strike plate 54.

As shown in FIGS. 1 and 2, the illustrative body 50 includes a grip configured receive the hand of a surgeon or other user to allow the user to manipulate the handle 48. Accordingly, parts of the body 50 may be coated in a rubberized or textured material to improve grip stability. In some embodiments, the body 50 may be assembled from multiple units including the grip.

As shown, the instrument handle 48 includes the distal strike plate 54, which is attached to a distal end of the body 50. The strike plate 54 is securely attached to the rest of the handle 48, for example by mechanically threading onto the end of the grip of the body 50. The strike plate 54 includes a durable distal surface 62 suitable for use with a striking tool such as a mallet, sledge, or other impaction tool. The distal surface 62 is large enough to cover the grip in order to shield the hand of the user. In use, the surgeon may impact the strike plate 54 to advance the broach 26 into the medullary canal of the patient's femur. The surgeon may impact an underside surface 64 of the strike plate 54 to remove the broach 26 from the patient's femur.

The illustrative handle 48 includes a detachable broach stop 66 connected to the body 50. The broach stop 66 is configured to provide visual, tactile, or other feedback to allow the surgeon to determine when the broach 26 has been advanced to the correct position in the patient's femur. For example, the illustrative broach stop 66 includes a base plate that defines a substantially planar proximal surface that may be used by the surgeon to seat the broach 26 at the proper depth in the patient's medullary canal. The broach stop 66 may be attached to one of multiple mounting positions on the body 50 to adjust the target depth for the broach 26.

Figure 4:
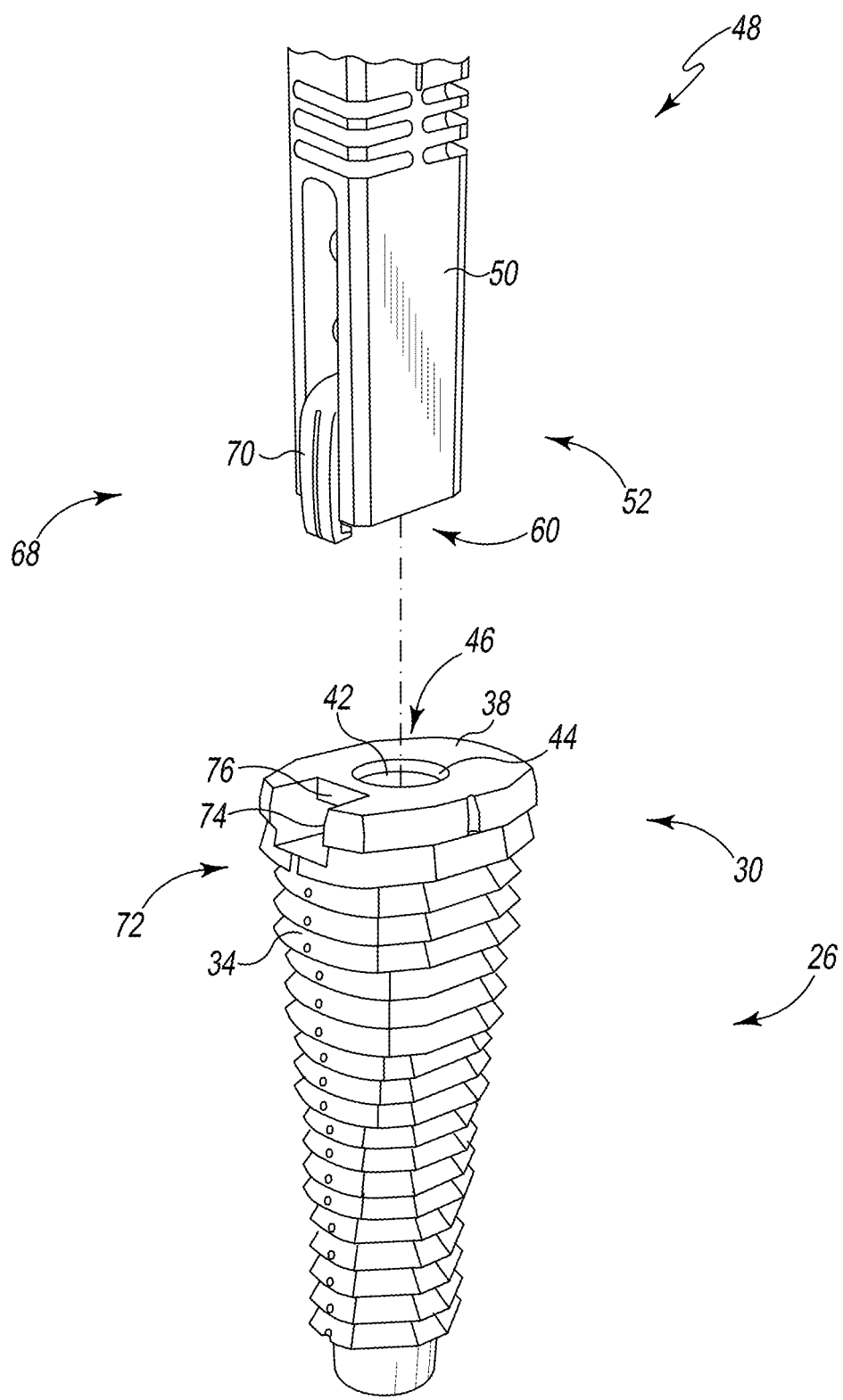

The handle 48 further includes an attachment mechanism 68 that is configured to secure the broach 26 to the instrument handle 48. Referring now to FIG. 4, one embodiment of the attachment mechanism 68 is shown. As shown, the attachment mechanism 68 includes a spring-loaded hook 70 that extends outwardly from the proximal end 52 of the handle 48. The distal end 30 of the broach 26 has a slot 72 defined therein. The slot 72 extends inwardly from the outer surface 34 through the distal surface 38 to a side wall 74. A flange 76 extends from the side wall 74 into the slot 72. As shown, the flange 76 is positioned adjacent to the aperture 44. When the broach 26 is secured to the handle 48, the hook 70 of the attachment mechanism 68 engages the flange 76 and retains the broach 26 against the handle 48. When the broach 26 is attached to the handle 48, the apertures 44, 56 and the bores 46, 60 align, allowing the shaft 22 of the reamer 12 to slide through the broach 26 and into the handle 48. The broach 26 is released from the handle 48 when the hook 70 disengages the flange 76, for example when a surgeon operates a lever to disengage the hook 70.

Figure 3:
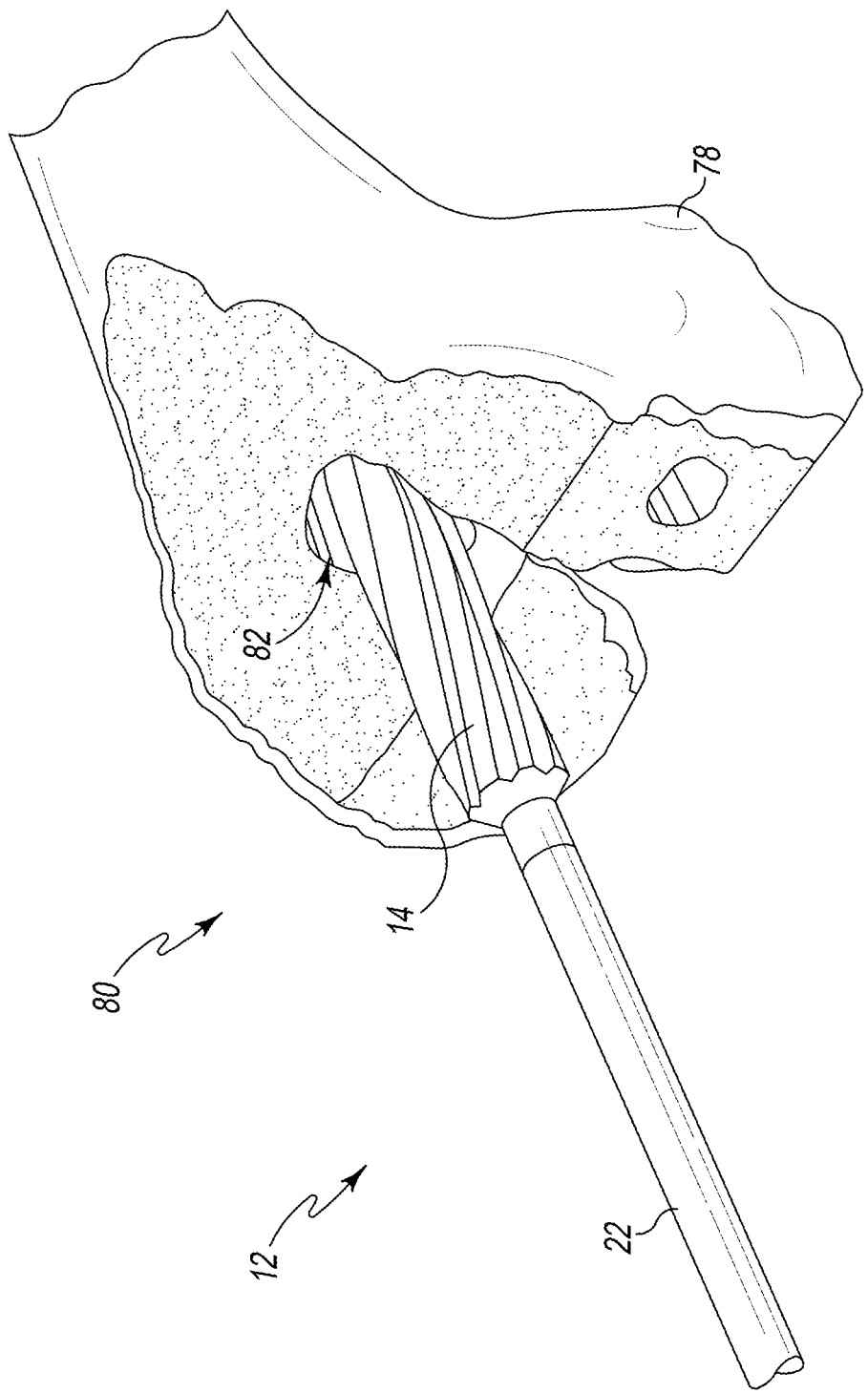
FIGS. 3-5 are views of a patient's femur and the orthopaedic surgical instrument system of FIGS. 1-2 as the orthopaedic surgical instrument system is used in a procedure.
Figure 5:
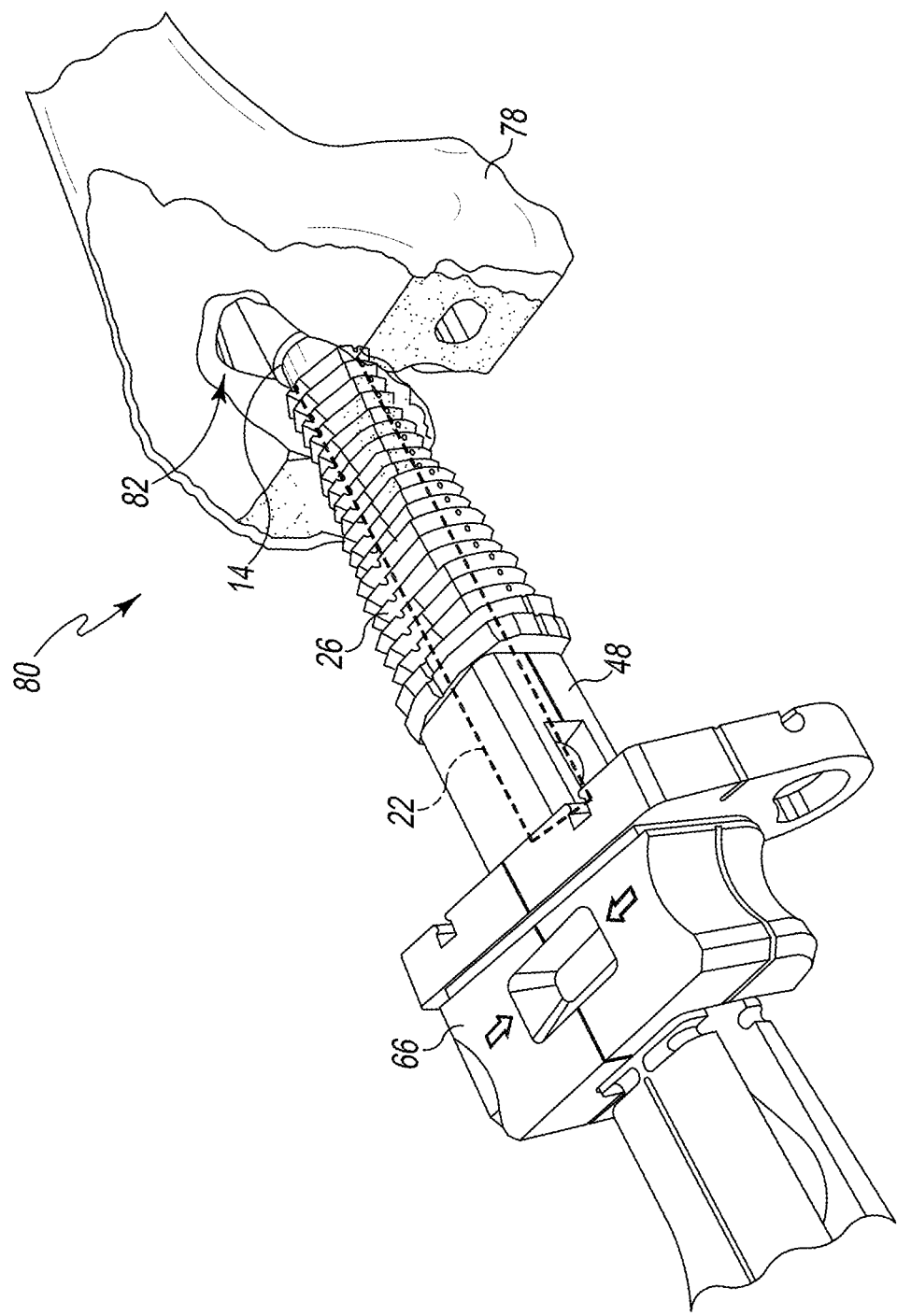

The instrument assembly 10 may be utilized during the performance of an orthopaedic surgical procedure similar to that shown in FIGS. 3-5. A surgeon initially prepares a distal end 80 of a patient's femur 78, for example by resecting the distal surface of the femur 78 and opening the medullary canal 82. The surgeon then inserts the surgical reamer 12 into the medullary canal 82, as shown in FIG. 3. The surgeon may use the reamer 12 to drill and/or ream the medullary canal 82 to the depth and/or diameter required to receive the broach 26. Multiple drills or reamers may be used to increase the size of the opening of the medullary canal formed on the distal end of the patient's femur. When the reaming operation is complete, the medullary canal 82 is ready to receive the broach 26. The reamer 12 remains positioned in the medullary canal 82.

After preparing the medullary canal 82, the surgeon secures the broach 26 to the handle 48 as shown in FIG. 4. As described above, when the surgeon attaches the proximal end 52 of the handle 48 to the distal end 30 of the broach 26, the hook 70 of the attachment mechanism 68 engages the flange 76 and retains the broach 26 against the handle 48.

Next, as shown in FIG. 5, the surgeon slides the bore 46 of the broach 26 over the shaft 22 of the reamer 12 and advances the broach 26 into the medullary canal 82. Depending on the length of the shaft 22 and the depth of the reamer 12 in the medullary canal 82, the bore 60 of the handle 48 may also slide over the shaft 22. The surgeon may then drive the broach 26 into the femur 78 by striking the strike plate 54 of the instrument handle 48 with mallet, sledge, or other impaction tool. The shaft 22 of the reamer 12 guides and stabilizes the broach 26 as it advances into the bone. As the broach 26 is driven into the bone, the cutting teeth 38 of the broach 26 engage the patient's femur 78 to shape the medullary canal 82 to receive the prosthetic femoral component or a femoral trial component. The surgeon may advance the broach 26 into the medullary canal 82 until the broach 26 is correctly in position, for example, when the broach stop 66 engages the distal surface 80 of the femur 78. After broaching, the surgeon may remove the broach 26 and repeat broaching with a different broach 26, for example with progressively larger broaches 26 until rotational stability is achieved.

After the final broach 26 is in position and any resection is complete, the surgeon may further prepare the medullary canal 82 and the femur 78 to receive a prosthetic implant. The surgeon may release the instrument handle 48 from the broach 26 and remove the instrument handle 48. After removing the instrument handle 48, the broach 26 and the reamer 12 remain seated within the medullary canal 82. To continue preparation, the surgeon may attach one or more other instruments to the broach 26 and/or reamer 12, such as cutting guides, adapters, trial components, or other instruments.

After completing preparation of the patient's femur 78, the surgeon may reattach the instrument handle 48 to the broach 26 and remove the broach 26 from the medullary canal 82. After removing the broach 26, the surgeon may also remove the reamer 12 from the medullary canal 82. After removal, the surgeon may proceed with implantation of prosthetic components.

Referring now to FIGS. 6-12, a modular femoral broach 100 is shown. The modular broach 100 includes multiple broach segments 102 that may be attached together by a surgeon to form the broach 100. As described further below, the surgeon may select different broach segments 102 to assemble the broach 100, and the size (e.g., length and diameter) of the assembled broach 100 is determined by the included broach segments 102. By allowing the surgeon to assemble a modular broach 100 from broach segments 102, the modular broach 100 may be used in place of multiple broaches of different sizes. For example, the modular broach 100 may be used with the instrument system 10 in place of multiple cannulated broaches 26 as described above in connection with FIGS. 1-5. Each broach segment 102 is typically smaller than a complete broach; thus, the modular broach 100 may save size, weight, and/or cost as compared to sets of complete broaches.

Figure 6:
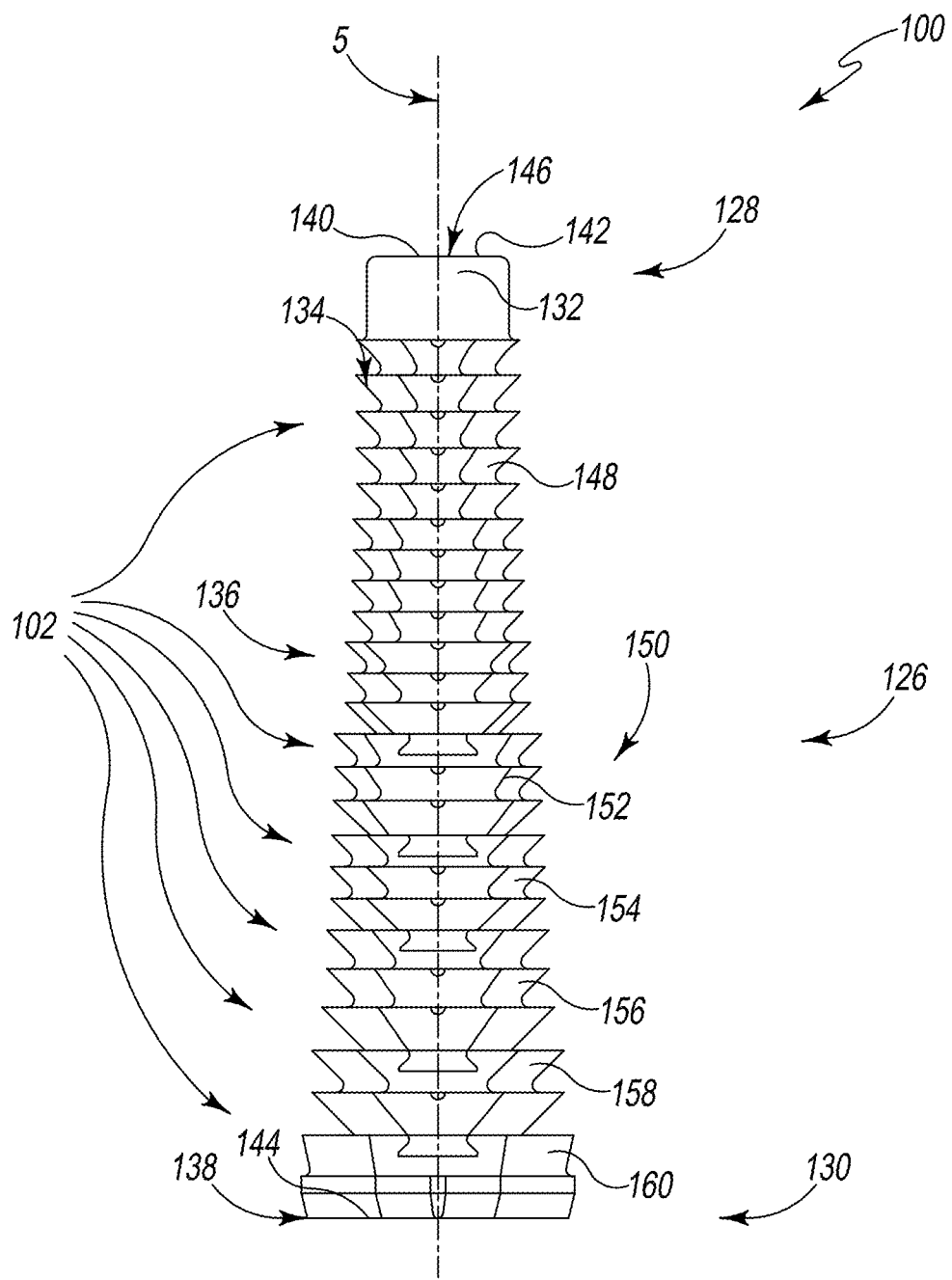
FIG. 6 is an elevation view of a modular broach that may be used with the orthopaedic surgical instrument system of FIGS. 1-2.

As shown in FIG. 6, the assembled, modular broach 100 is illustratively a femoral broach configured to be positioned in the medullary canal 82 of the patient's femur. The illustrative broach 100 includes an outer surface 134 extending from a proximal end 128 to a distal end 130. The outer surface 134 is tapered, with the diameter of the broach 126 increasing from the proximal end 128 to the distal end 130.

A plurality of cutting teeth 136 are formed on the outer surface 134 between the proximal end 128 and the distal end 130. Similar to the broach 26 described above, the cutting teeth 136 are configured to engage the bone surrounding the medullary canal 82 when the broach 100 is inserted therein.

The broach 100 includes a boss 132 positioned at the proximal end 128, and a substantially planar distal surface 138 positioned at the distal end 130 thereof. The boss 132 at the proximal end 128 has a circular aperture 140 defined therein, and a circular aperture 144 is defined in the distal surface 138. An inner wall 142 extends between the proximal end 128 and the distal end 130, and defines the apertures 140, 144. Accordingly, the inner wall 142 defines a bore 146 that extends through the broach 100 from the proximal end 128 to the distal end 130. Similar to the bore 46 of the broach 26, the bore 146 of the broach 100 is sized to receive and slide over the shaft 22 of the reamer 12.

Figure 7:
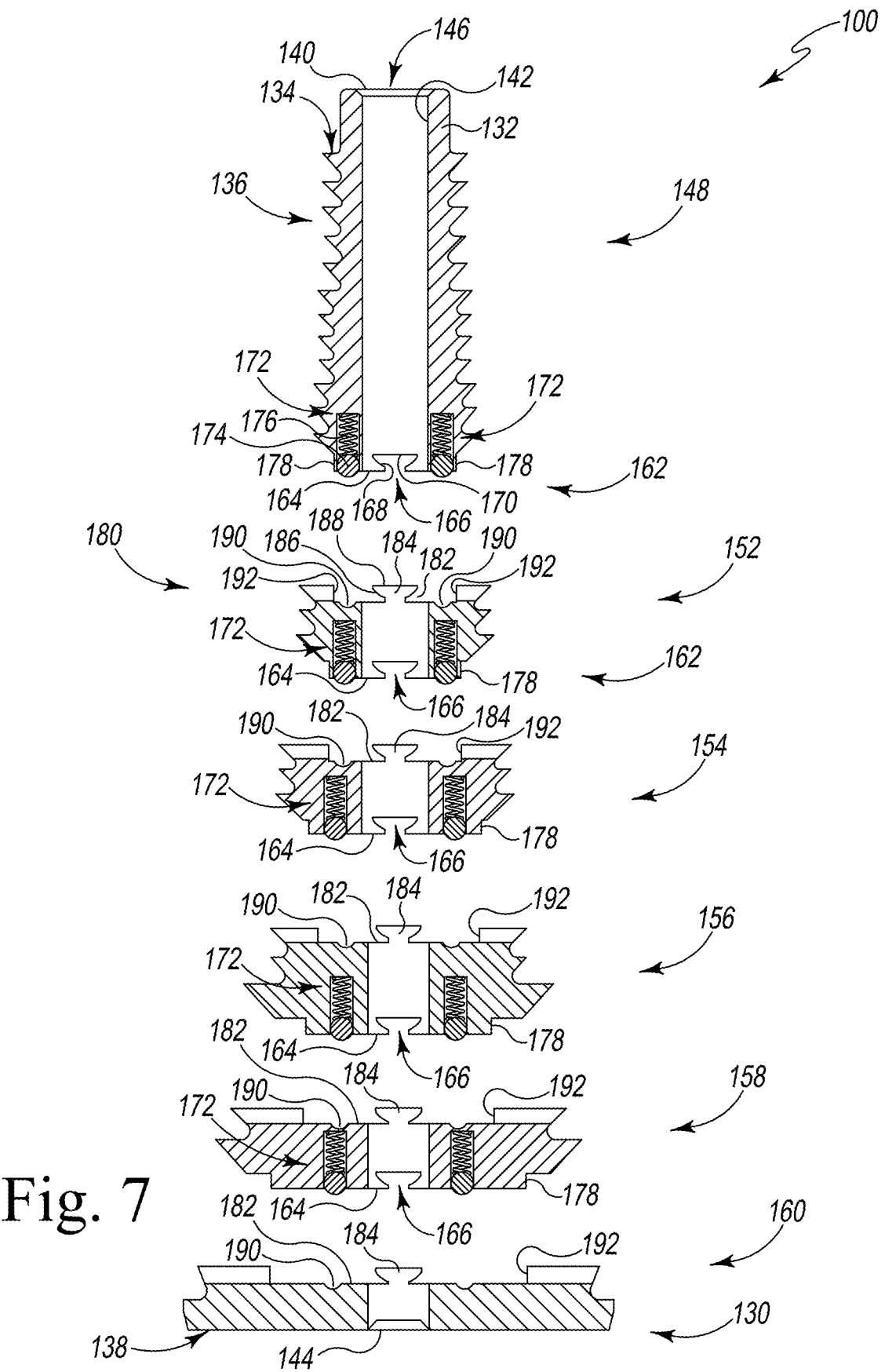
FIG. 7 is an exploded cross-sectional view of the modular broach of FIG. 6.

As shown in FIGS. 6-7, the broach segments 102 of the broach 100 include a proximal broach segment 148, multiple middle broach segments 150, and a distal broach segment 160. The broach 100 illustratively includes four middle broach segments 152, 154, 156, 158; however, in other embodiments, the broach 100 may include other numbers of middle broach segments 150. Each of the broach segments 102 includes a tapered outer surface 134 and a plurality of cutting teeth 136 formed on the outer surface 134. The segments 102 increase in diameter progressively from the proximal segment 148 through the middle segments 152, 154, 156, 158 to the distal segment 160.

As shown in FIG. 7, the proximal segment 148 extends from the proximal end 128 of the broach 100 to a distal end 162 of the proximal segment 148. An aperture 164 is defined in the distal end 162. The inner wall 142 extends between the proximal end 128 and the distal end 162 and defines the apertures 140, 164. Accordingly, the bore 146 extends through the proximal segment 148 from the proximal end 128 to the distal end 162.

A dovetail slot 166 is defined in the distal end 162 of the proximal segment 148. An inner wall 168 extends from the distal end 162 inward to a slot bottom 170 to define the dovetail slot 166. As shown, the dovetail slot 166 is wider at the slot bottom 170 than at the distal end 162.

The proximal segment 148 further includes a pair of ball detents 172 positioned at the distal end 162. Each ball detent 172 includes a ball 174 and a spring 176. The spring 176 biases the ball 174 to extend outward from the proximal end 162. When the spring 176 is compressed, the ball 174 may be retracted within the proximal segment 148. Each of the ball detents 172 is adjacent to an outer shoulder 178, which is a flat part of the outer surface 134 that does not include the cutting teeth 136.

Similar to the proximal segment 148, the middle segment 152 extends from a proximal end 180 to a distal end 162. An aperture 182 is defined in the proximal end 180, and an aperture 164 is defined in the distal end 162. The inner wall 142 extends between the proximal end 180 and the distal end 162 and defines the apertures 182, 164. Accordingly, the bore 146 extends through the middle segment 152 from the proximal end 180 to the distal end 162.

The proximal end 180 includes a dovetail 184. The dovetail 184 extends outwardly from a base 186 attached to the proximal end 180 to a free end 188. The free end 188 is wider than the base 186 such that the dovetail 184 is sized and shaped to be received within the dovetail slot 166 of the proximal segment 148. A pair of recesses 190 are further defined in the proximal end 180. Each recess 190 is sized to receive a ball 174 of a ball detent 172. The proximal end 180 further includes an inner shoulder 192 adjacent to each recess 190. As described further below, when the segments 148, 152 are attached, the dovetail 184 is retained within the dovetail slot 166, and the ball detents 172 cooperate with the recesses 190 to align the aperture 182 of the middle segment 152 with the aperture 164 of the proximal segment 148.

Similar to the proximal segment 148, a dovetail slot 166 is defined in the distal end 162 of the middle segment 152. An inner wall 168 extends from the distal end 162 inward to a slot bottom 170 to define the dovetail slot 166. As shown, the dovetail slot 166 is wider at the slot bottom 170 than at the distal end 162.

Also similar to the proximal segment 148, the middle segment 152 further includes a pair of ball detents 172 positioned at the distal end 162. Each ball detent 172 includes a ball 174 and a spring 176. The spring 176 biases the ball 174 to extend outward from the proximal end 162. When the spring 176 is compressed, the ball 174 may be retracted within the middle segment 152. Each of the ball detents 172 is adjacent to an outer shoulder 178, which is a flat part of the outer surface 134 that does not include the cutting teeth 136.

As shown in FIG. 7, each of the other middle segments 154, 156, 158 includes components similar to the middle segment 152, including a dovetail 184, a dovetail slot 166, ball detents 172, and part of the bore 146. The description of those components is not repeated herein so as not to obscure the present disclosure.

Similar to each of the middle segments 150, the distal segment 160 extends from a proximal end 180 to the distal end 130. An aperture 182 is defined in the proximal end 180. The inner wall 142 extends between the proximal end 180 and the distal end 130 and defines the apertures 182, 144. Accordingly, the bore 146 extends through the distal segment 160 from the proximal end 180 to the distal end 130.

The proximal end 180 of the distal segment 160 includes a dovetail 184. The dovetail 184 extends outwardly from a base 186 attached to the proximal end 180 to a free end 188. The free end 188 is wider than the base 186 such that the dovetail 184 is sized and shaped to be received within the dovetail slot 166 of the middle segment 158. A pair of recesses 190 are further defined in the proximal end 180. Each recess 190 is sized to receive a ball 174 of a ball detent 172. The proximal end 180 further includes an inner shoulder 192 adjacent to each recess 190. As described further below, when the segments 158, 160 are attached, the dovetail 184 is retained within the dovetail slot 166, and the ball detents 172 cooperate with the recesses 190 to align the aperture 182 of the distal segment 160 with the aperture 164 of the middle segment 158. Note that the illustrative distal segment 160 does not include a dovetail slot or ball detents.

As shown in FIGS. 8-12, the broach segments 102 may be combined to assemble modular broaches 100 of varying sizes. Each combination of broach segments 102 shown in FIGS. 8-12 may have the same size or other outer geometry as a corresponding broach 26 of a set of broaches 26 as described above in connection with the instrument system 10. Of course, it should be noted that the proximal segment 148 may be used as a broach 100 without attaching any other broach segments 102. In that circumstance, the proximal segment 148 may have the same size as the smallest broach 26 of the set of broaches 26.

Figure 8:
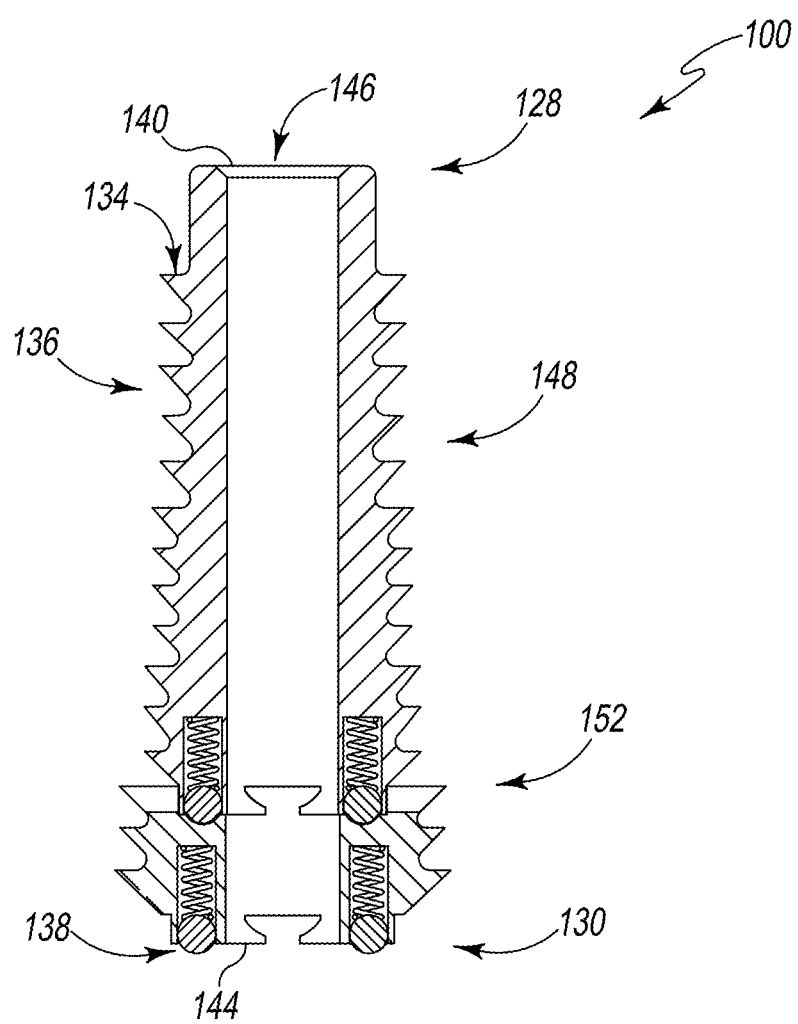
FIGS. 8-12 are cross-sectional views of possible configurations of the modular broach of FIGS. 6-7.

Referring now to FIG. 8, the middle broach segment 152 may be attached to the proximal broach segment 148. The segments 148, 152 may be attached by sliding the dovetail 184 of the middle broach segment 152 into the dovetail slot 166 of the proximal segment 148. As the segments 148, 152 are attached, the outer shoulder 178 of the proximal segment 148 engages the inner shoulder 192 of the middle segment 152. The dovetail 184 is slid into the dovetail slot 166 until the ball detents 172 of the proximal segment 148 engage the recesses 190 of the middle segment 152. As shown in FIG. 8, when the broach segments 148, 152 are attached, the bore 146 extends through the segments 148, 152, and the tapered outer surface 134 extends along the segments 148, 152. As shown, the outer surface 134 widens from the proximal end 128 of the proximal segment 148 to the distal end 130 of the middle segment 152.

Figure 9:
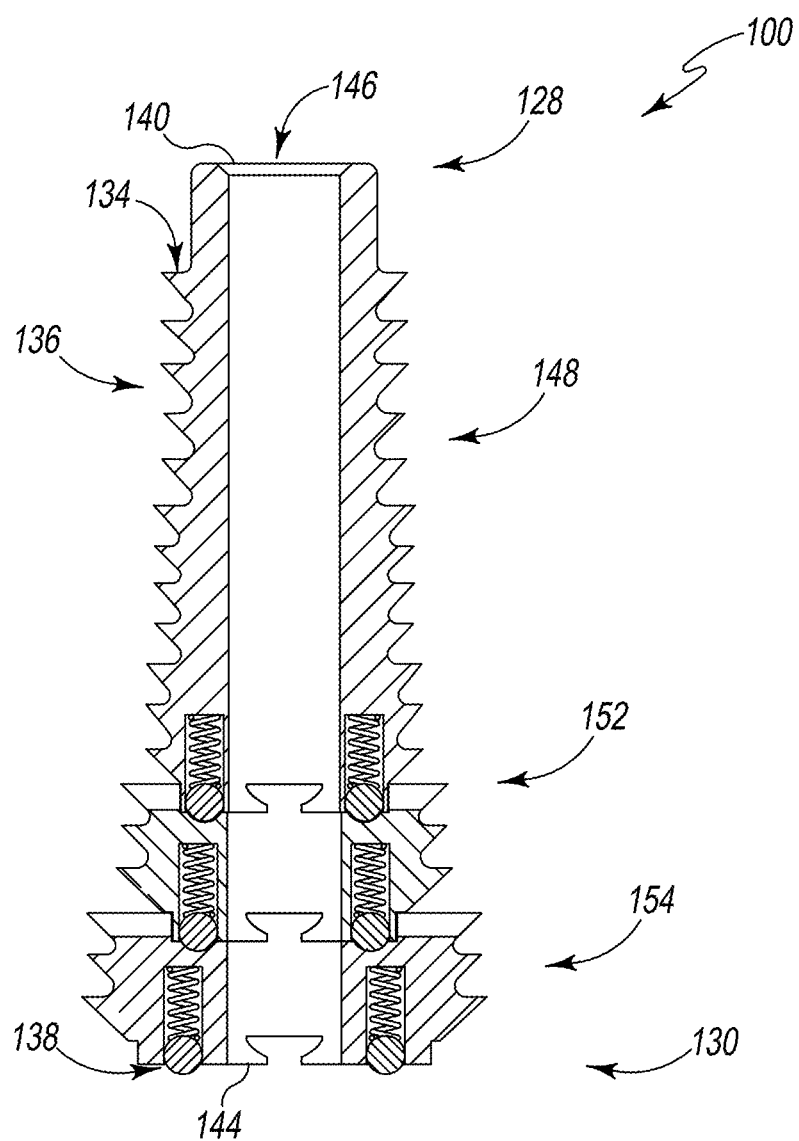

Referring now to FIG. 9, the middle broach segment 154 may be attached to the broach segments 148, 152. The segment 154 may be attached to the segments 148, 152 by sliding the dovetail 184 of the broach segment 154 into the dovetail slot 166 of the broach segment 152. As the segments 152, 154 are attached, the outer shoulder 178 of the broach segment 152 engages the inner shoulder 192 of the broach segment 154. The dovetail 184 is slid into the dovetail slot 166 until the ball detents 172 of the broach segment 152 engage the recesses 190 of the broach segment 154. As shown in FIG. 9, when the broach segments 148, 152, 154 are attached, the bore 146 extends through the segments 148, 152, 154 and the tapered outer surface 134 extends along the segments 148, 152, 154. As shown, the outer surface 134 widens from the proximal end 128 of the proximal segment 148 to the distal end 130 of the broach segment 154.

Figure 10:
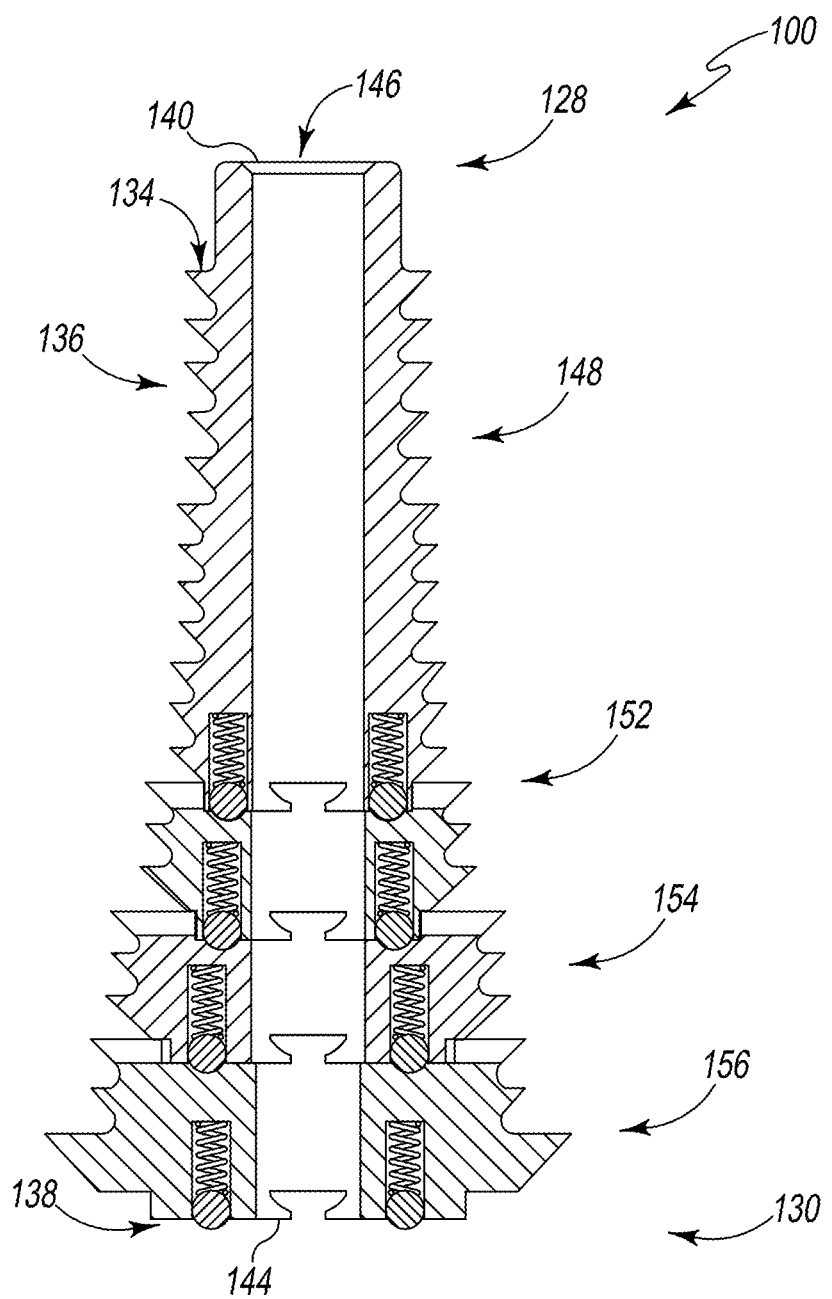

Referring now to FIG. 10, the middle broach segment 156 may be attached to the broach segments 148, 152, 154. The segment 156 may be attached to the segments 148, 152, 154 by sliding the dovetail 184 of the broach segment 156 into the dovetail slot 166 of the broach segment 154. As the segments 154, 156 are attached, the outer shoulder 178 of the broach segment 154 engages the inner shoulder 192 of the broach segment 156. The dovetail 184 is slid into the dovetail slot 166 until the ball detents 172 of the broach segment 154 engage the recesses 190 of the broach segment 156. As shown in FIG. 10, when the broach segments 148, 152, 154, 156 are attached, the bore 146 extends through the segments 148, 152, 154, 156 and the tapered outer surface 134 extends along the segments 148, 152, 154, 156. As shown, the outer surface 134 widens from the proximal end 128 of the proximal segment 148 to the distal end 130 of the broach segment 156.

Figure 11:
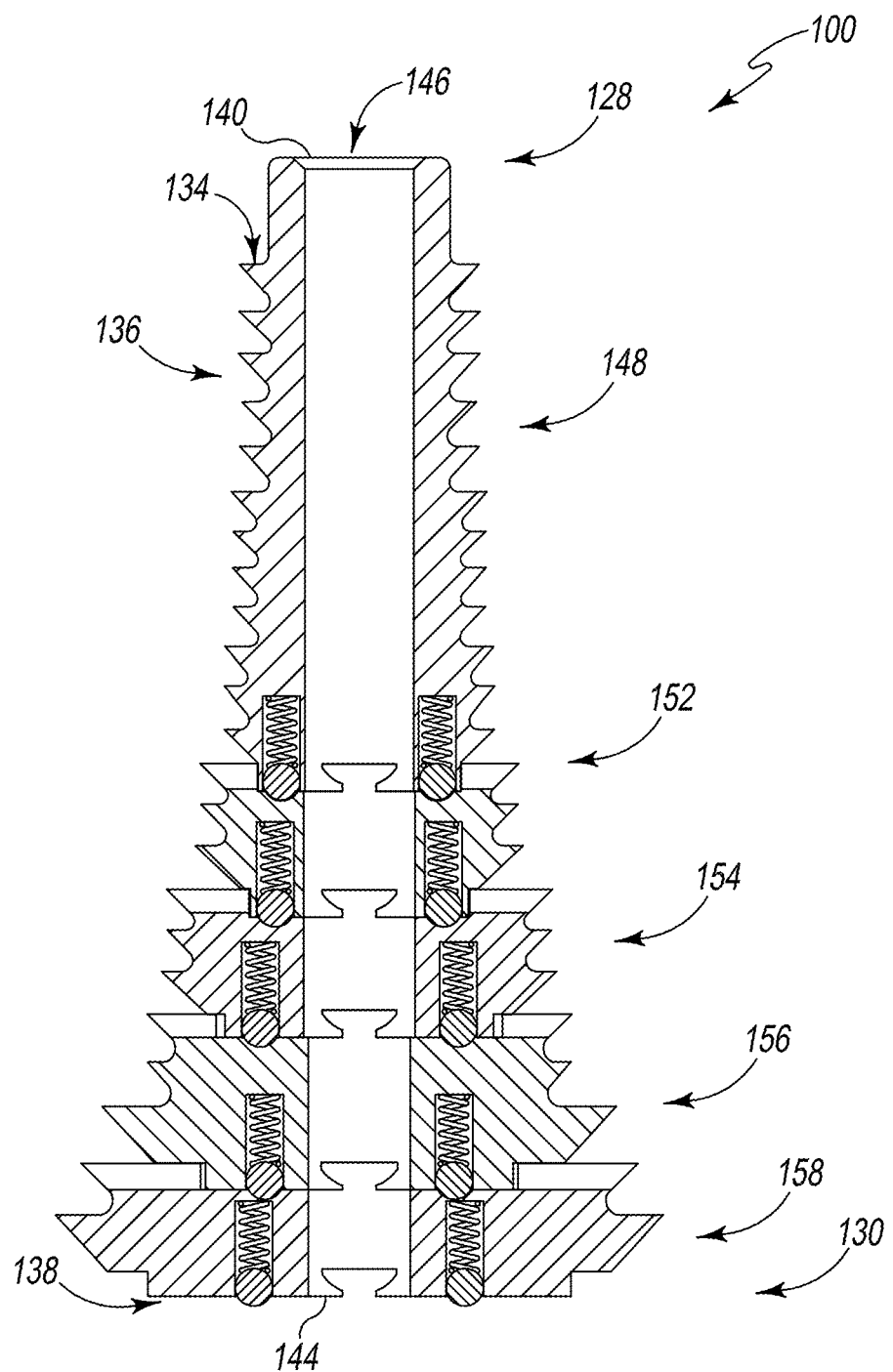

Referring now to FIG. 11, the middle broach segment 158 may be attached to the broach segments 148, 152, 154, 156. The segment 158 may be attached to the segments 148, 152, 154, 156 by sliding the dovetail 184 of the broach segment 158 into the dovetail slot 166 of the broach segment 156. As the segments 156, 158 are attached, the outer shoulder 178 of the broach segment 156 engages the inner shoulder 192 of the broach segment 158. The dovetail 184 is slid into the dovetail slot 166 until the ball detents 172 of the broach segment 156 engage the recesses 190 of the broach segment 158. As shown in FIG. 11, when the broach segments 148, 152, 154, 156, 158 are attached, the bore 146 extends through the segments 148, 152, 154, 156, 158 and the tapered outer surface 134 extends along the segments 148, 152, 154, 156, 158. As shown, the outer surface 134 widens from the proximal end 128 of the proximal segment 148 to the distal end 130 of the broach segment 158.

Figure 12:
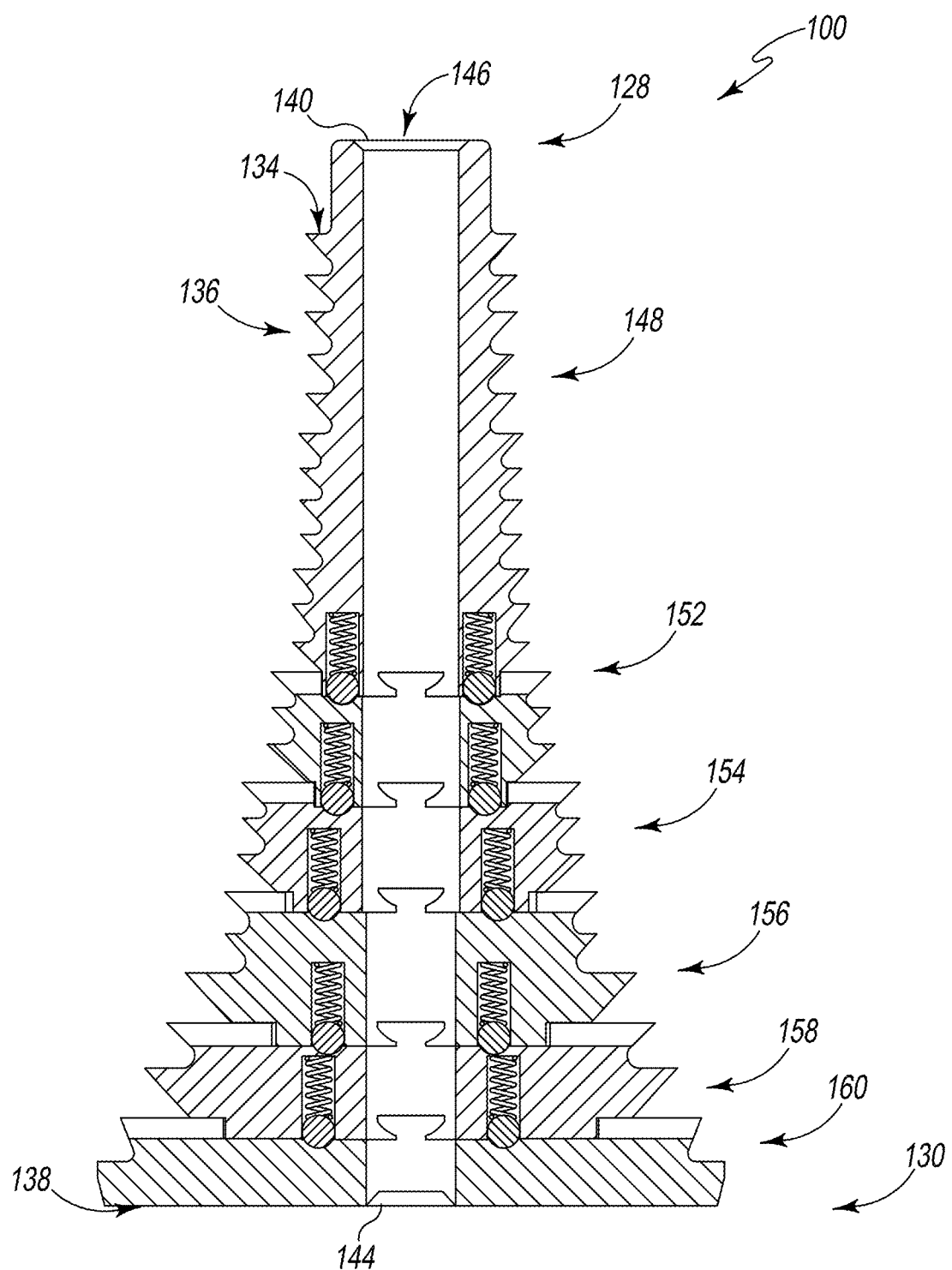

Referring now to FIG. 12, the distal broach segment 160 may be attached to the broach segments 148, 152, 154, 156, 158. The segment 160 may be attached to the segments 148, 152, 154, 156, 158 by sliding the dovetail 184 of the broach segment 160 into the dovetail slot 166 of the broach segment 158. As the segments 158, 160 are attached, the outer shoulder 178 of the broach segment 158 engages the inner shoulder 192 of the broach segment 160. The dovetail 184 is slid into the dovetail slot 166 until the ball detents 172 of the broach segment 158 engage the recesses 190 of the broach segment 160. As shown in FIG. 12, when the broach segments 148, 152, 154, 156, 158, 160 are attached, the bore 146 extends through the segments 148, 152, 154, 156, 158, 160 and the tapered outer surface 134 extends along the segments 148, 152, 154, 156, 158, 160. As shown, the outer surface 134 widens from the proximal end 128 of the proximal segment 148 to the distal end 130 of the broach segment 160.

The modular broach 100 may be utilized during the performance of an orthopaedic surgical procedure similar to that shown in FIGS. 3-5. As described above and as shown in FIG. 3, the surgeon may prepare the medullary canal 82 of the patient's femur 78 by reaming the medullary canal with the reamer 12. When the reaming operation is complete, the medullary canal 82 is ready to receive the broach 100, and the reamer 12 remains positioned in the medullary canal 82.

After preparing the medullary canal 82, the surgeon may select a combination of broach segments 102 and assemble the modular broach 100 having a desired size. In the illustrative embodiment, the surgeon may assemble a modular broach 100 having one of six possible sizes. In particular, the surgeon may select the proximal segment 148 alone or may select among the five combinations of segments 102 shown in FIGS. 8-12. The surgeon may assemble the modular broach 100 by attaching the segments 102 as described above in connection with FIGS. 8-12.

After selecting and/or assembling the modular broach 100, the surgeon secures the modular broach 100 to the handle 48, similar to the procedure shown in FIG. 4. Next, similar to the procedure shown in FIG. 5, the surgeon slides the bore 146 of the broach 100 over the shaft 22 of the reamer 12 and advances the broach 100 into the medullary canal 82. Depending on the length of the shaft 22 and the depth of the reamer 12 in the medullary canal 82, the bore 60 of the handle 48 may also slide over the shaft 22. The surgeon may then drive the broach 100 into the femur 78 by striking the strike plate 54 of the instrument handle 48 with mallet, sledge, or other impaction tool. The shaft 22 of the reamer 12 guides and stabilizes the broach 100 as it advances into the bone. The shaft 22 also stabilizes the segments 102 of the broach relative to each other as the broach 100 advances along the shaft 22. As the broach 100 is driven into the bone, the cutting teeth 38 of the broach 100 engage the patient's femur 78 to shape the medullary canal 82 to receive the prosthetic femoral component or a femoral trial component. The surgeon may advance the broach 100 into the medullary canal 82 until the broach 100 is correctly in position, for example, when the broach stop 66 engages the distal surface 80 of the femur 78. After broaching, the surgeon may remove the broach 100 and repeat broaching with a different configuration of the modular broach 100. For example, the surgeon may attach one or more additional segments 102 to the broach 100 to progressively increase the size of the broach 100 until rotational stability is achieved.

Additionally or alternatively, in some embodiments, additional broach segments 102 may be attached to the modular broach 100 without removing the broach 100 from the medullary canal 82. In those embodiments, the broach segments 102 may include an attachment mechanism other than the dovetail 184 and dovetail slot 166 arrangement of the illustrative embodiment. For example, the broach segments 102 may include a hook and flange arrangement similar to the handle 48 and broach 26 of FIGS. 1-5.

In those embodiments, the surgeon may advance the broach 100 into the medullary canal 82 until the broach 100 is in position, for example, when the broach stop 66 engages the distal surface 80 of the femur 78. The surgeon may detach the handle 48 from the broach 100 and remove the handle 48. After removing the handle 48, the reamer 12 and the broach 100 remain in the medullary canal 82, and the shaft 22 extends out of the distal end 130 of the broach 100. The surgeon selects the next-larger broach segment 102 to attach to the broach 100. For example, after the proximal segment 148 has been positioned in the medullary canal 82, the surgeon may select the middle segment 152, after the middle segment 152 has been positioned in the medullary canal 82, the surgeon may select the middle segment 154, and so on. The surgeon slides the bore 146 of the selected broach segment 102 over the shaft 22 of the reamer 12 and advances the broach segment 102 to attach to the broach 100. The surgeon may then attach the handle 48 to the newly extended distal end 130 of the modular broach 100 and continue broaching the medullary canal 82. Thus, in those embodiments, the surgeon may progressively enlarge the medullary canal 82 without removing the broach 100 from the canal 82.

As described above, after the final configuration of the broach 100 is in position and any resection is complete, the surgeon may further prepare the medullary canal 82 and the femur 78 to receive a prosthetic implant. The surgeon may release the instrument handle 48 from the broach 100 and remove the instrument handle 48. After removing the instrument handle 48, the broach 100 and the reamer 12 remain seated within the medullary canal 82. To continue preparation, the surgeon may attach one or more other instruments to the broach 100 and/or reamer 12, such as cutting guides, adapters, trial components, or other instruments.

After completing preparation of the patient's femur 78, the surgeon may reattach the instrument handle 48 to the broach 100 and remove the broach 100 from the medullary canal 82. After removing the broach 100, the surgeon may also remove the reamer 12 from the medullary canal 82. After removal, the surgeon may proceed with implantation of prosthetic components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument assembly, comprising:
   a first broach segment including a tapered body extending from a proximal end to a distal end, the tapered body having a plurality of cutting teeth defined therein, the first broach segment including a ball detent positioned on the distal end, wherein a dovetail slot is defined in the distal end; and
   a second broach segment including a tapered body extending from a proximal end to a distal end, the tapered body having a plurality of cutting teeth defined therein, wherein the proximal end of the second broach segment is removably coupled to the distal end of the first broach segment, the second broach segment including a dovetail positioned on the proximal end, wherein a recess is defined in the proximal end;
   wherein when coupled the first broach segment and the second broach segment cooperate to define a bore that extends from a first aperture defined in the proximal end of the first broach segment to a second aperture defined in the distal end of the second broach segment, wherein the bore is sized to slide over a shaft of a surgical reamer; and
   wherein when coupled the tapered body of the first broach segment and the tapered body of the second broach segment form a tapered outer surface that widens from the proximal end of the first broach segment to the distal end of the second broach segment;
   wherein the dovetail slot defined in the first broach segment is sized to receive the dovetail of the second broach segment, and the recess defined in the second broach segment is sized to receive the ball detent of the first broach segment.

2. The orthopaedic surgical instrument assembly of claim 1, wherein the distal end of the first broach segment and the distal end of the second broach segment are each configured to be removably attached to a surgical instrument handle.

3. The orthopaedic surgical instrument assembly of claim 1, further comprising:
   a third broach segment including a tapered body extending distally from a proximal end to a distal end, the tapered body having a plurality of cutting teeth defined therein, wherein the proximal end of the third broach segment is removably coupled to the distal end of the second broach segment;
   wherein when the third broach segment is coupled to the second broach segment, the bore further extends to an aperture defined in the distal end of the third broach segment, and the tapered body of the third broach segment extends the tapered outer surface that widens from the proximal end of the first broach segment to the distal end of the third broach segment.

4. The orthopaedic surgical instrument assembly of claim 3, further comprising:
   a fourth broach segment including a tapered body extending distally from a proximal end to a distal end, the tapered body having a plurality of cutting teeth defined therein, wherein the proximal end of the fourth broach segment is removably coupled to the distal end of the third broach segment;
   wherein when the fourth broach segment is coupled to the third broach segment, the bore further extends to an aperture defined in the distal end of the fourth broach segment, and the tapered body of the fourth broach segment extends the tapered outer surface that widens from the proximal end of the first broach segment to the distal end of the fourth broach segment.

5. The orthopaedic surgical instrument assembly of claim 4, further comprising:
   a fifth broach segment including a tapered body extending distally from a proximal end to a distal end, the tapered body having a plurality of cutting teeth defined therein, wherein the proximal end of the fifth broach segment is removably coupled to the distal end of the fourth broach segment;
   wherein when the fifth broach segment is coupled to the fourth broach segment, the bore further extends to an aperture defined in the distal end of the fifth broach segment, and the tapered body of the fifth broach segment extends the tapered outer surface that widens from the proximal end of the first broach segment to the distal end of the fifth broach segment.

6. The orthopaedic surgical instrument assembly of claim 5, further comprising:
   a sixth broach segment including a tapered body extending distally from a proximal end to a distal end, the tapered body having a plurality of cutting teeth defined therein, wherein the proximal end of the sixth broach segment is removably coupled to the distal end of the fifth broach segment;
   wherein when the sixth broach segment is coupled to the fifth broach segment, the bore further extends to an aperture defined in the distal end of the sixth broach segment, and the tapered body of the sixth broach segment extends the tapered outer surface that widens from the proximal end of the first broach segment to the distal end of the sixth broach segment.

* * * * *